US010551320B2

(12) United States Patent
Haller

(10) Patent No.: US 10,551,320 B2
(45) Date of Patent: Feb. 4, 2020

(54) ACTIVATION OF WAFER PARTICLE DEFECTS FOR SPECTROSCOPIC COMPOSITION ANALYSIS

(71) Applicant: KLA-Tencor Corporation, Milpitas, CA (US)

(72) Inventor: Kurt L. Haller, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 193 days.

(21) Appl. No.: 15/419,355

(22) Filed: Jan. 30, 2017

(65) Prior Publication Data

US 2018/0217065 A1   Aug. 2, 2018

(51) Int. Cl.
*G01N 21/65*   (2006.01)
*G01N 21/94*   (2006.01)
*G01N 21/95*   (2006.01)

(52) U.S. Cl.
CPC ............. *G01N 21/65* (2013.01); *G01N 21/94* (2013.01); *G01N 21/9501* (2013.01)

(58) Field of Classification Search
CPC ......... G01N 21/65; G01N 21/94; G01N 21/95
USPC ...... 422/82.05; 436/73, 80–81, 84, 164, 171
See application file for complete search history.

(56) References Cited

U.S. PATENT DOCUMENTS

| | | | |
|---|---|---|---|
| 4,978,862 A * | 12/1990 | Silva | G01N 21/9505 250/225 |
| 5,608,526 A | 3/1997 | Piwonka-Corle et al. | |
| 5,715,052 A * | 2/1998 | Fujino | G01N 21/94 356/237.2 |
| 5,859,424 A | 1/1999 | Norton et al. | |
| 5,943,552 A * | 8/1999 | Koveshnikov | H01L 22/12 257/E21.53 |

(Continued)

FOREIGN PATENT DOCUMENTS

JP   2011-009554 A   1/2011

OTHER PUBLICATIONS

Baufay, L. et al, Materials Research Society Proceedings 1987, 75, 281-287.*

(Continued)

*Primary Examiner* — Arlen Soderquist
(74) *Attorney, Agent, or Firm* — Spano Law Group; Joseph S. Spano

(57) ABSTRACT

Methods and systems for detecting a particle defect on a wafer surface, transforming the particle to a spectroscopically active state, and identifying a material composition of the activated particle by a spectroscopic technique are described herein. Particle defects are transformed by chemical treatment, thermal treatment, photochemical treatment, or a combination thereof, such that an activated particle exhibits atomic vibrational bands that can be observed spectroscopically. In one embodiment, a surface inspection system detects the presence of a particle defect on a wafer surface, activates observable Raman bands in one or more of the detected particles, and identifies the material composition of the activated particle by a spectroscopic technique. By performing both defect detection and composition analysis on the same inspection tool, it is not necessary to transfer a wafer to a different review tool, or combination of tools, to perform composition analysis of particle defects deposited on semiconductor wafers.

19 Claims, 8 Drawing Sheets

(56) References Cited

U.S. PATENT DOCUMENTS

| | | | |
|---|---|---|---|
| 6,067,154 A * | 5/2000 | Hossain | G01N 21/65 356/237.2 |
| 6,201,601 B1 | 3/2001 | Vaez-Lravani et al. | |
| 6,208,411 B1 | 3/2001 | Vaez-Lravani | |
| 6,271,916 B1 | 8/2001 | Marxer et al. | |
| 6,429,943 B1 | 8/2002 | Opsal et al. | |
| 6,545,755 B1 * | 4/2003 | Ishihama | G01J 3/44 356/237.3 |
| 7,130,039 B2 | 10/2006 | Vaez-Lravani et al. | |
| 7,295,303 B1 | 11/2007 | Vaez-Lravani et al. | |
| 7,433,056 B1 * | 10/2008 | Janik | G01B 11/0616 356/301 |
| 7,478,019 B2 | 1/2009 | Zangooie et al. | |
| 7,777,876 B2 | 8/2010 | Horai et al. | |
| 7,933,026 B2 | 4/2011 | Opsal et al. | |
| 8,169,613 B1 * | 5/2012 | Biellak | G01J 1/0422 356/237.2 |
| 9,007,581 B2 | 4/2015 | Horai et al. | |
| 2002/0109110 A1 * | 8/2002 | Some | G01N 21/9501 250/559.4 |
| 2002/0159052 A1 * | 10/2002 | Klooster | G01N 21/9501 356/237.2 |
| 2003/0168594 A1 * | 9/2003 | Muckenhirn | G01N 21/4788 250/307 |
| 2004/0106217 A1 * | 6/2004 | Higgs | G01N 21/6489 438/5 |
| 2005/0037615 A1 * | 2/2005 | Cabib | G01J 3/44 438/689 |
| 2005/0274805 A1 * | 12/2005 | Ramappa | H01L 22/20 235/462.07 |
| 2006/0038980 A1 * | 2/2006 | Naka | G01N 21/65 356/73 |
| 2006/0262296 A1 * | 11/2006 | Higgs | G01N 21/6489 356/237.3 |
| 2007/0132987 A1 * | 6/2007 | Haller | G01N 21/9501 356/237.2 |
| 2007/0176119 A1 * | 8/2007 | Hummel | G01B 11/24 250/458.1 |
| 2007/0229809 A1 * | 10/2007 | Belyaev | G01N 21/9501 356/237.2 |
| 2008/0084555 A1 * | 4/2008 | Yoo | G01J 3/36 356/73 |
| 2008/0129988 A1 | 6/2008 | Saito et al. | |
| 2008/0151259 A1 * | 6/2008 | Yoo | G01N 21/9501 356/521 |
| 2008/0218741 A1 * | 9/2008 | Murtagh | G01N 21/1717 356/73 |
| 2009/0009753 A1 * | 1/2009 | Horai | G01N 21/65 356/237.3 |
| 2009/0009754 A1 * | 1/2009 | Haller | G01N 21/9501 356/237.5 |
| 2009/0047748 A1 * | 2/2009 | Savtchouk | H01L 22/14 438/17 |
| 2011/0292376 A1 * | 12/2011 | Kukushkin | G01J 1/58 356/73 |
| 2012/0127467 A1 | 5/2012 | Ivanov | |
| 2013/0050689 A1 | 2/2013 | Reich et al. | |
| 2014/0111791 A1 | 4/2014 | Manassen et al. | |
| 2014/0118729 A1 * | 5/2014 | Wolters | G01N 21/9501 356/237.5 |
| 2014/0146297 A1 | 5/2014 | Vainer | |
| 2014/0172394 A1 | 6/2014 | Kuznetsov et al. | |
| 2014/0222380 A1 | 8/2014 | Kuznetsov et al. | |
| 2014/0226140 A1 * | 8/2014 | Chuang | G02B 17/0892 355/67 |
| 2015/0268176 A1 * | 9/2015 | Deng | G01N 21/9501 250/372 |

OTHER PUBLICATIONS

Baufay, L. et al, Journal of Applied Physics 1987, 61, 4640-4651.*
Herman, I. P. et al, Materials Research Society Proceedings 1991, 201, 563-572.*
De Wolf, I., Semiconductor Science and Technology 1996, 11, 139-154.*
Takami, K., Materials Science and Engineering 1997, B44, 181-187.*
Ramappa, D. A., Applied Physics Letters 2000, 76, 3756-3758.*
Ballast, L. K. et al, AIP Conference Proceedings 2001, 550, 327-331.*
Vainola, H. et al, Journal of the Electrochemical Society 2003, 150, G790-G794.*
Bonse, J. et al, Applied Surface Science 2004, 221, 215-230.*
Grenon, B. J. et al, SPIE 2004, 5375, 355-362.*
Belayachi, A. et al, Applied Physics A 2005, 80, 201-204.*
Trushin, M. et al, Nuclear Instruments and Methods in Physics Research B 2010, 268, 254-258.*
Kar, A. et al, Journal of Physical Chemistry C 2011, 115, 118-124.*
Pena-Rodriguez, O. et al, Journal of the Optical Society of America B 2011, 28, 2735-2739.*
Levitskii, V. S. et al, Technical Physics Letters 2015, 41, 1094-1096.*
Wu, C.-Y. et al, Nature 2017, 541, 511-515 and supplementary materials.*
Zhu, Yongfu et al., "Brief Review of Oxidation Kinetics of Copper at 350C to 1050C," Metallurgical and Materials Transactions A, vol. 37A, Apr. 2006, pp. 1231-1237.
Zhu, Yongfu et al., "Oxidation Mechanism of Copper at 623-1073K," Materials Transactions, vol. 43, No. 9 (2002), pp. 2173-2176.
Nerle, Uma et al., "Thermal Oxidation of Copper for Favorable Formation of Cupric Oxide (CuO) Semiconductor," IOSR Journal of Applied Physics, vol. 5, Issue 1 (Nov.-Dec. 2013), pp. 1-7.
Demirkiran, Nizamettin, "Preparation of Cupric Oxide by Isothermal Oxidation of Metallic Copper Powder Produced by Elecroless Deposition," Russian Journal of Non-Ferrous Metals, vol. 55, No. 6 (2014), pp. 529-532.
Zhidovinova, S.V., "Oxidation of Copper Ultrafine Powders and Nanopowders Produced by Vapor Phase Condensation," Russian Metallurgy, vol. 2010, Issue 9, Sep. 2010, pp. 774-778, Abstract only submitted.
Setoura, Kenji et al., "Observation of Nanoscale Cooling Effects by Substrates and the Surrounding Media for Single Gold Nanoparticles under CW-Laser Illumination," American Chemical Society Nano, vol. 7, No. 8, (2013), pp. 7874-7885.
Setoura, Kenji et al., Supporting Information for Setoura article listed as citation No. 6.
International Search Report dated May 11, 2018, for PCT Application No. PCT/US2016/015570 filed on Jan. 26, 2018 by KLA-Tencor Corporation, 3 pages.

* cited by examiner

ACTIVATION OF WAFER PARTICLE DEFECTS FOR SPECTROSCOPIC COMPOSITION ANALYSIS

TECHNICAL FIELD

The described embodiments relate to systems for surface inspection, and more particularly to semiconductor wafer inspection modalities.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

One such inspection system illuminates and inspects an unpatterned wafer surface for undesired particles. As semiconductor design rules continue to evolve, the minimum particle size that must be detected by a surface inspection system continues to shrink in size.

Integrated circuit yield loss due to particle contamination from wafer processing equipment must be remediated to realize a cost effective manufacturing process. In a semiconductor fabrication facility, particle contamination levels are monitored by an unpatterned wafer surface inspection system such as the Surfscan® family of products manufactured by KLA-Tencor Corporation, Milpitas, Calif. (USA). A typical contamination metric measured by the inspection tool is the number of particles-per-wafer-pass (PWP). By comparing defect maps measured before and after a test wafer passes through a process tool, the number of added defects is periodically measured and tracked. When PWP exceeds control chart limits, the offending process tool is taken offline to investigate the root cause of the excursion and resolve the problem.

Traditionally, a database of normal and out-of-control defect compositions is generated during the development of the manufacturing processes associated with a particular technology node. During development, scanning electron microscope (SEM) images of added particles are compiled. However, in many cases defect images alone do not positively identify defect types and origins. Thus, in addition, the spectra of characteristic X-rays emitted by particles under electron bombardment are measured with an energy dispersive X-ray (EDX) spectrometer to identify constituent elements.

Subsequently, when excursions occur during high volume manufacturing, an out-of-control test wafer is measured using SEM and EDX tools. The data is compared with the database generated during process development. The measured distribution of defect compositions is compared with the database of past excursions to identify the root cause of the problem. Actions are taken to return the tool to production based on this knowledge.

In general, it is much easier to solve the contamination problem when the chemical composition of the offending particles is known. However, it is a time consuming process to obtain composition measurement results in high volume production environments, where review of patterned wafers by SEM and EDX tools is typically prioritized ahead of review of unpatterned wafers. In addition, review by SEM and EDX tools that are separate from the particle defect review tool requires movement of the wafer from one tool to another, which costs time.

RAMAN spectroscopy is a potential analytical technique that may be employed to identify the composition of particle defects on a wafer surface. U.S. Pat. Nos. 7,777,876 and 9,007,581 issued to Hitachi High-Technologies Corporation describe a surface inspection system that detects both elastic and inelastic scattered light (i.e., Rayleigh and Raman scattering, respectively). A spectrometer is employed to resolve solid-state vibrational modes in the inelastic light, revealing composition information, although it is does not appear to the inventor that any of the reported measurements correspond to Raman spectra from actual particle defects that might be generated by an integrated circuit process tool.

Although atomic vibrational bands of some particles can be observed with laser Raman microspectroscopy, in general, there are many important defect particles of interest (i.e., materials of interest) that do not exhibit active Raman vibrational bands, and are thus unobservable by Raman spectroscopic techniques.

Improvements to scanning surface inspection systems are desired to both detect the presence of defects on the wafer surface and identify the material composition of detected defect particles without transferring the wafer to a different review tool.

SUMMARY

Methods and systems for detecting a particle defect on a wafer surface, transforming the particle to a spectroscopically active state, and identifying a material composition of the activated particle by a spectroscopic technique are described herein. Particle defects are transformed by chemical treatment, thermal treatment, photochemical treatment, or a combination thereof, such that an activated particle exhibits atomic vibrational bands that can be observed spectroscopically.

Many defect particles generated by semiconductor manufacturing equipment and processes are spectroscopically inactive. For example, metallic nanoparticles having body centered cubic (bcc) or face centered cubic (fcc) crystal symmetry have no observable Raman spectral lines.

In one aspect, a scanning surface inspection system detects the presence of a particle defect on a wafer surface, activates observable Raman bands in one or more of the detected particles, and identifies the material composition of the activated particle by a spectroscopic technique. By performing both defect detection and composition analysis on the same inspection tool, it is not necessary to transfer a wafer to a different review tool, or combination of tools, to perform composition analysis of particle defects deposited on semiconductor wafers.

A computing system is configured to receive spectroscopic measurement results collected from an activated particle and estimate a composition of the particle based on the measurements. In some embodiments, the computing system matches the spectroscopic signature of the measured spectra (e.g., peak locations, peak magnitudes, etc.) with the signature of reference spectra measured from particles having a known composition. In some embodiments, the computing system matches the spectroscopic signature of the measured spectra with the signature of analytically derived spectra. In some embodiments, the computing system correlates the spectroscopic signature of the measured spectra with a library database of previously analyzed defect particles. In some embodiments, the library includes optical spectroscopic response data. In some further embodiments, the library also includes other composition data (e.g., photoluminescence data, energy dispersive X-ray (EDX) spectrometer data, etc.).

In a further aspect, the composition of a defect particle is determined based on the measurement of photoluminescence (PL) spectra. In some examples, defect particles exhibit broadband photoluminescence (PL) spectra extending as far as the near IR.

In another further aspect, the collected light is cross-polarized with respect to the illumination light to improve the signal to noise ratio of the detected signals.

In some embodiments, a surface inspection system is employed to generate a map of defect locations on the wafer surface in a scanning mode to rapidly generate a defect mapping of the entire wafer surface or significant portions of the wafer surface. After mapping the wafer surface, the surface inspection system is employed to activate and analyze one or more of the defect particles previously detected by the defect particle detection subsystem. In some other embodiments, a defect particle is activated and analyzed immediately after detection.

In some examples, the activation of the particle is due to a chemical oxidation of a metallic particle. In some examples, the transformation of the particle occurs in a chamber of controlled partial pressure of oxygen. In some examples, the chamber includes additional partial pressures of substantially inert gases that do not participate in the oxidation process. In some examples, the chamber includes additional partial pressures of gaseous compounds that catalyze the oxidative transformation.

In some examples, a metallic particle is treated with a surface-active material before oxidation to promote formation of the metallic oxide with oxidation state and crystalline polymorphic structure having an enhanced Raman scattering cross section.

In some examples, the oxidative transformation is driven by elevated temperature. In some examples, the elevated temperature may be generated by radiative heating, illumination with electromagnetic radiation, or a combination thereof.

In some examples, the oxidative transformation of a particle is driven by a photochemical pathway stimulated by exposure to photons emitted from an electromagnetic radiation source.

In some examples, the transformation is a chemical reaction, other than an oxidative reaction, with gaseous, liquid, or solution-borne reagents and a photothermal or photochemical driving force.

In general, multiple, different illumination sources may be employed to provide illumination for activation, spectral measurement, or both. In addition, one or more illumination sources employed to map the locations of defect particles on the wafer surface may also be employed to provide illumination for activation, spectral measurement, or both.

In some examples, multiple, different wavelengths are employed and the wavelengths are selected because they are known to interact with surface asperities of the substrate wafer (e.g., thin films, high aspect ratio protrusions of highly non-spherical defect particles, etc.). The surface asperities produce enhanced electromagnetic fields in their immediate vicinity that enhance weak spectroscopic signatures.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for detecting a particle defect on a wafer surface, transforming the particle to a spectroscopically active state, and identifying a material composition of the activated particle by a spectroscopic technique are described herein.

The inventive concepts described herein are based on the observation that many defect particles generated by semiconductor manufacturing equipment and processes are spectroscopically inactive (e.g., particles do not have atomic vibrational bands that can be observed with Raman spectroscopy). However, by chemical treatment, thermal treatment, photochemical treatment, or a combination thereof, particle defects are transformed such that an activated particle exhibits atomic vibrational bands that can be observed spectroscopically (e.g., via Raman spectroscopy).

In one aspect, a scanning surface inspection system detects the presence of a particle defect on a wafer surface, activates observable Raman bands in one or more of the detected particles, and identifies the material composition of the activated particle by a spectroscopic technique. By performing both defect detection and composition analysis on the same inspection tool, it is not necessary to transfer a wafer to a different review tool, or combination of tools, to perform composition analysis of particle defects deposited on semiconductor wafers.

Figure 1:
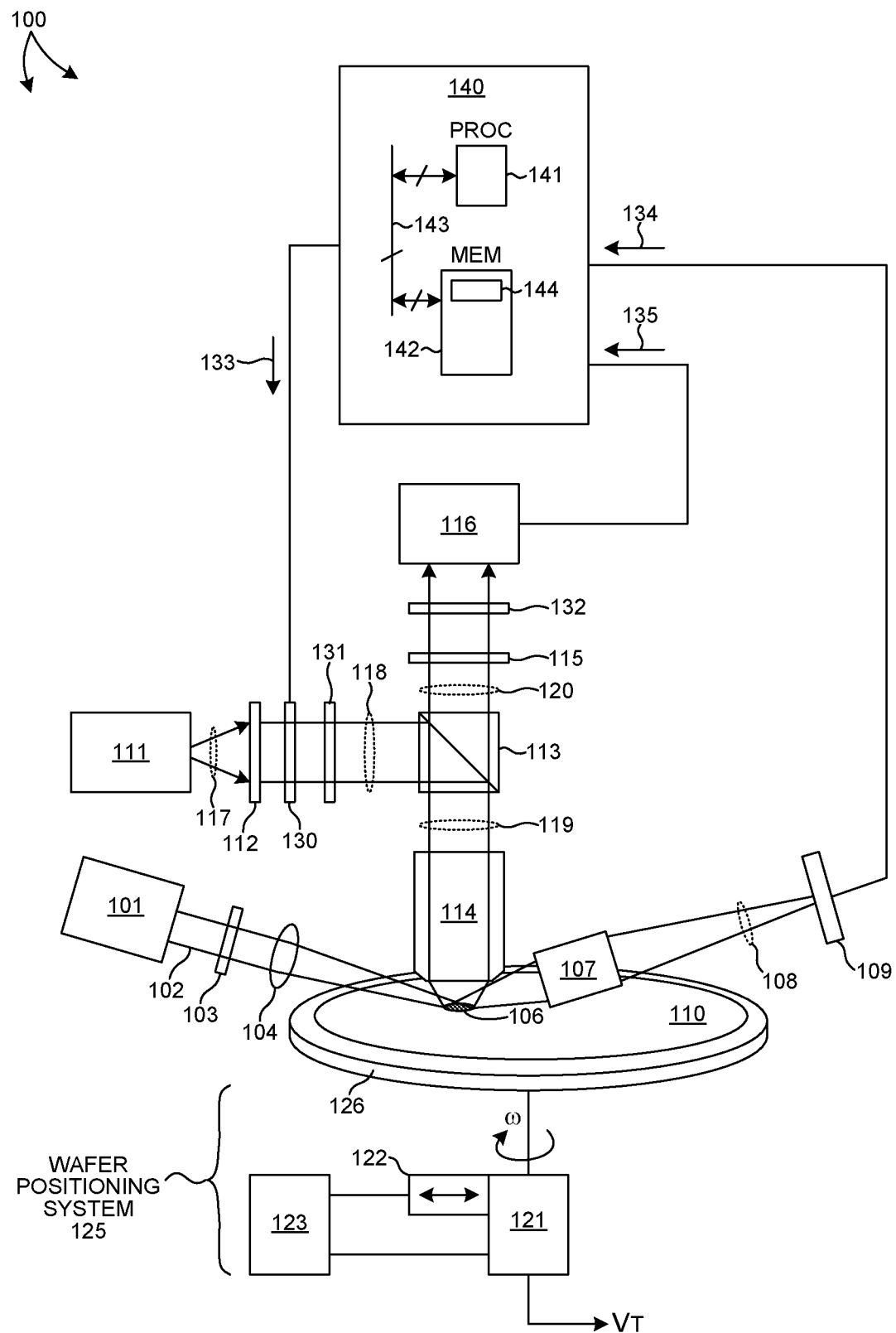
FIG. 1 is a simplified diagram illustrative of one embodiment of an inspection system configured to detect, activate, and identify the material composition of a defect particle on a specimen under inspection.

FIG. 1 is a simplified schematic view of one embodiment of a surface inspection system 100 that may be used to perform the inspection methods described herein. For simplification, some optical components of the system have been omitted. By way of example, folding mirrors, polarizers, beam forming optics, additional light sources, additional collectors, and additional detectors may also be included. All such variations are within the scope of the invention described herein. The inspection system described herein may be used for inspecting patterned, as well as unpatterned wafers.

As illustrated in FIG. 1, surface inspection system 100 includes a defect particle detection subsystem including illumination source 101, optical elements 103, 104, and 107, and detector 109. In addition surface inspection system 100 includes a defect particle activation and analysis subsystem including illumination source 111, optical elements 112-115, 130-132, and detector 116.

Illumination source 101 of the defect particle detection subsystem generates a beam of illumination light 102 that is directed toward wafer 110. As depicted in FIG. 1, illumination is provided to the surface of wafer 110 at an oblique angle by the defect particle detection subsystem. However, in general, the defect particle detection subsystem may be configured to direct the beam of light to the specimen at a normal angle of incidence. In some embodiments, the defect particle detection subsystem may be configured to direct multiple beams of light to the specimen at different angles of incidence, such as an oblique angle and a normal angle of incidence. The multiple beams of light may be directed to the specimen substantially simultaneously or sequentially.

Illumination source 101 may include, by way of example, a laser, a diode laser, a helium neon laser, an argon laser, a solid state laser, a diode pumped solid state (DPSS) laser, a xenon arc lamp, a gas discharging lamp, and LED array, or an incandescent lamp. The light source may be configured to emit near monochromatic light or broadband light. In some embodiments, the defect particle detection subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm) for an interval of time. Therefore, if the light source is a broadband light source, the defect particle detection subsystem may also include one or more spectral filters that may limit the wavelength of the light directed to the specimen. The one or more spectral filters may be bandpass filters and/or edge filters and/or notch filters. In some embodiments, the defect particle detection subsystem is configured to direct light to the specimen having a very narrow wavelength band suitable for Raman spectroscopy. In some examples, the linewidth of the illumination has a linewidth on the order of 30 gigahertz (1 cm$^{-1}$), or less. In one example, a laser illumination source is configured to emit light at 405 nanometers with a linewidth of less than 0.016 nanometers.

In some embodiments, a constant power laser beam is generated by illumination source 101, and an illumination power control element 103 is employed to regulate beam power to prevent damage to the wafer surface. In some embodiments, beam power is regulated based on the size and material composition of the particles being scanned.

After passing through illumination power control element 103, the illumination beam is directed to illumination optics 104 that focus the beam of illumination light 102 onto the wafer surface. In general, the light that reaches the surface of the wafer may be altered in one or more ways, including polarization, intensity, size and shape, etc.

Figure 2:
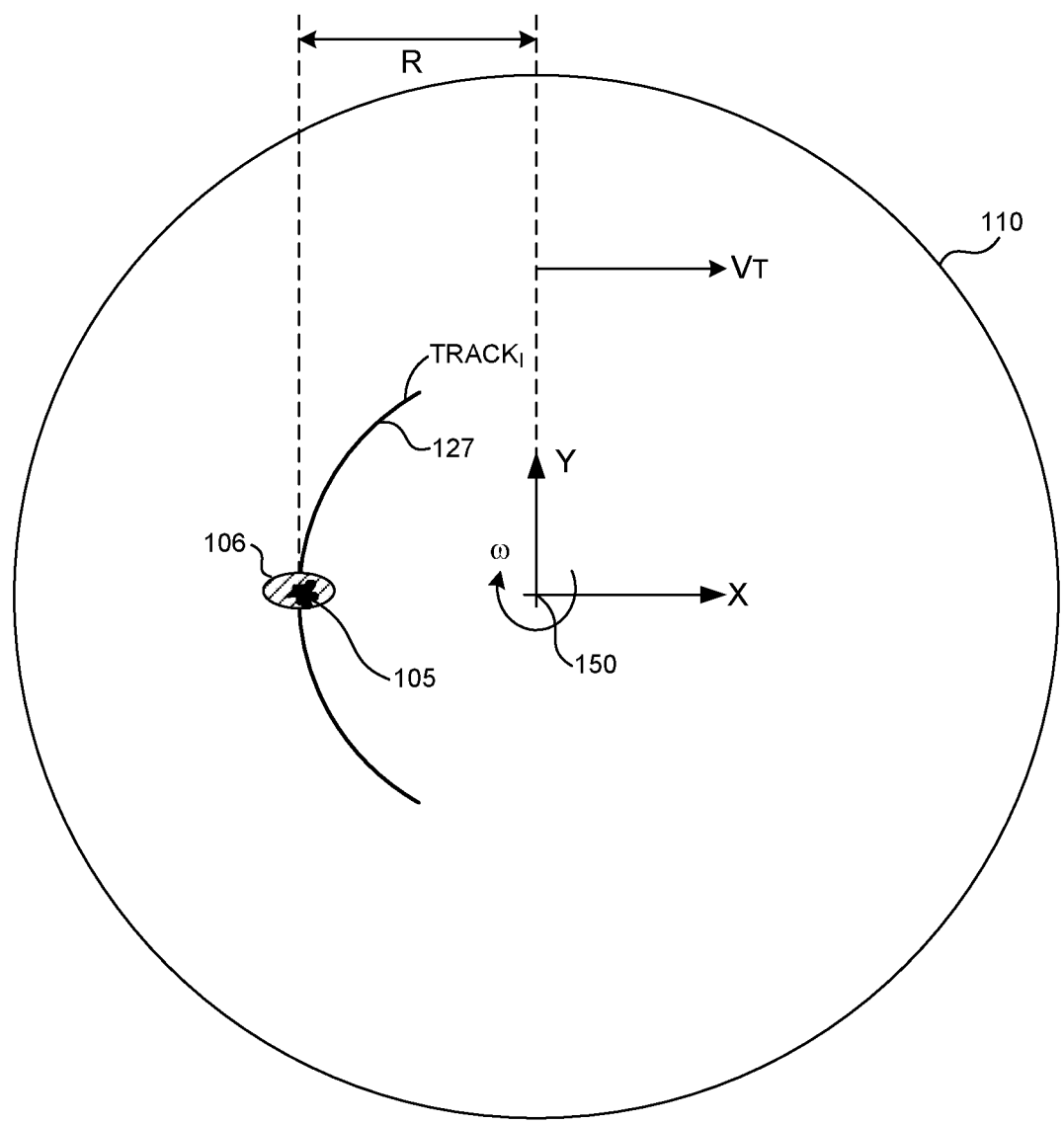
FIG. 2 is a diagram illustrative of a top view of wafer positioned on a rotary scanning stage.

In the embodiment illustrated in FIG. 1, wafer positioning system 125 moves wafer 110 under illumination beam 102 to adjust the location of the measurement spot 106 on the wafer surface. Wafer positioning system 125 includes a wafer chuck 126, motion controller 123, a rotation stage 121 and a translation stage 122. Wafer 110 is supported on wafer chuck 126. As illustrated in FIG. 2, wafer 110 is located with its geometric center 150 approximately aligned the axis of rotation of rotation stage 121. In this manner, rotation stage 121 spins wafer 110 about its geometric center at a specified angular velocity, ω, within an acceptable tolerance. In addition, translation stage 122 translates the wafer 110 in a direction substantially perpendicular to the axis of rotation of rotation stage 121 at a specified velocity, $V_T$. Motion controller 123 coordinates the spinning of wafer 110 by rotation stage 121 and the translation of wafer 110 by translation stage 122 to achieve the desired scanning motion of wafer 110 within inspection system 100.

In an exemplary operational scenario, inspection begins with measurement spot 106 located at the geometric center 150 of wafer 110 and then wafer 110 is rotated and translated until measurement spot 106 reaches the outer perimeter of wafer 110 (i.e., when R equals the radius of wafer 110). Due to the coordinated motion of rotation stage 121 and translation stage 122, the locus of points illuminated by measurement spot 106 trace a spiral path on the surface of wafer 110. The spiral path on the surface of wafer 110 is referred to as an inspection track 127 (not shown in its entirety). A portion of an exemplary inspection track 127 is illustrated in FIG. 2 as TRACK$_i$. As illustrated in FIG. 2, measurement spot 106 is located a distance, R, from the geometric center of wafer 150.

Collection optics 107 collect light scattered and/or reflected from measurement spot 106. Although a particular, nominal orientation of collection optics 107 is illustrated in FIG. 1, it is understood that the orientation of the collection optics with respect to the wafer surface may be arranged appropriately depending upon, for example, the angle of incidence and/or topographical characteristics of the wafer.

Light 108 collected by collection optics 107 is directed to detector 109. Detector 109 generally functions to convert the detected light into electrical signals indicative of the detected light collected from wafer 110 within the detected field of view. In general, detector 109 may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may be employed to increase the signal-to-noise ratio and throughput of the system. However, other detectors such as a photodiode, a phototube, a photomultiplier tube (PMT), a charge-coupled device (CCD) camera, arrays of photodiodes, phototubes and photomultiplier tubes (PMTS), may be used, depending on the amount of light available for inspection and the type of inspection being performed.

In some embodiments, detector 109 is a non-imaging detector configured to generate a single output signal indicative of the amount of light scattered from the measurement spot 106. A single output signal allows for efficient detection of large particles with high throughput.

In some embodiments, detector 109 is an imaging detector that may be implemented in various imaging modes, such as bright field, dark field, and confocal. Various imaging modes such as bright field, dark field, and phase contrast can be implemented by using different apertures or Fourier filters. U.S. Pat. Nos. 7,295,303 and 7,130,039, which are incorporated by reference herein, describe these imaging modes in further detail. In another example (not shown), a detector generates dark field images by imaging scattered light collected at larger field angles. In another example, a pinhole that matches the incident spot 106 can be placed in front of a detector (e.g., detector 109) to generate a confocal image. U.S. Pat. No. 6,208,411, which is incorporated by reference herein, describes these imaging modes in further detail. In addition, various aspects of surface inspection system 100 are described in U.S. Pat. Nos. 6,271,916 and 6,201,601, both of which are incorporated herein by reference.

In some embodiments, multiple detectors are selectably employed to detect light 108 collected from measurement spot 106. For example, one or more flip-in mirrors or beam splitters may be employed to selectably direct collected light 108 toward different detectors (e.g., one or more non-imaging detectors and one or more imaging detectors) to perform different defect particle measurements.

In at least one embodiment of the invention depicted in FIG. 1, a single detector (e.g., an individual photomultiplier tube (PMT)) is employed as detector 109 to detect light scattered from the measurement spot 106. The output signal 134 of detector 109 is communicated to a computing system 140 for processing to determine the presence of a defect particle.

In some embodiments, the defect particle detection subsystem of surface inspection system 100 is employed to generate a map of defect locations on the wafer surface. In these embodiments, the defect particle detection subsystem is operated in a scanning mode to rapidly generate a defect mapping of the entire wafer surface or significant portions of the wafer surface. After mapping the wafer surface, the defect particle activation and analysis subsystem is employed to activate and analyze one or more of the defect particles previously detected by the defect particle detection subsystem. However, in some other embodiments, the defect particle activation and analysis subsystem is employed to activate and analyze a defect particle immediately after detection by the defect particle detection subsystem.

Illumination source 111 of the defect particle activation and analysis subsystem generates a beam of illumination light 117 that is directed toward wafer 110. As depicted in FIG. 1, illumination is provided to the surface of wafer 110 at multiple angles of incidence by the defect particle activation and analysis subsystem. However, in general, the defect particle activation and analysis subsystem may be configured to direct the beam of light to the specimen at any single angle of incidence or set of multiple angles of incidence, including a normal angle of incidence.

Illumination source 111 may include, by way of example, a laser, a diode laser, a helium neon laser, an argon laser, a solid state laser, a diode pumped solid state (DPSS) laser, a xenon arc lamp, a gas discharging lamp, and LED array, or an incandescent lamp. The light source may be configured to emit near monochromatic light or broadband light. In some embodiments, the defect particle activation and analysis subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm) for an interval of time. Therefore, if the light source is a broadband light source, the defect particle activation and analysis subsystem may also include one or more spectral filters 112 that may limit the wavelength of the light directed to the specimen. The one or more spectral filters may be bandpass filters and/or edge filters and/or notch filters. In some embodiments, the defect particle detection subsystem is configured to direct light to the specimen having a very narrow wavelength band suitable for Raman spectroscopy. In some examples, the linewidth of the illumination has a linewidth on the order of 30 gigahertz (1 cm$^{-1}$), or less. In one example, a laser illumination source is configured to emit light at 405 nanometers with a linewidth of less than 0.016 nanometers.

In the embodiment depicted in FIG. 1, illumination beam 117 is directed to illumination power control element 130. Illumination power control element 130 is configured to control the optical power of the beam of illumination light 117 in accordance with command signal 133 received from computing system 140. In one embodiment, illumination power control element 130 is located in the illumination beam path between illumination source 111 and beam splitting element 113 to dynamically adjust the illumination power during particle activation and analysis.

In a preferred embodiment, the illumination power control element 130 is a high efficiency, low cost, acousto-optic modulator (AOM). The optical power transmitted through the AOM is modulated by a radio frequency (RF) driver that provides fast switching capability without costly, high voltage drivers.

In general, illumination power control element 130 may be implemented with a selectively transmissive optical component, which may be adapted to transmit a portion of the incident light based on a polarization of the incident light. In some embodiments, illumination power control element 130 includes a wave plate (such as a quarter wave plate) and a polarizing beam splitter. In this configuration, the wave plate may be used to change the polarization of the incoming light, while the beam splitter functions to transmit one or more select polarizations (e.g., linearly polarized light) and reflect all others (e.g., randomly, circularly or elliptically polarized light). By reflecting portions of the light, the wave plate and beam splitter function to reduce the intensity or power level of the transmitted light.

In some embodiments, illumination power control element 130 includes an electro-optical material that is switchable between an "on" condition and an "off" condition. When "on," the electro-optical material changes the polarization of the incoming light into a predetermined polarization orientation. This so-called "re-polarized light" may then be supplied to a polarizing beam splitter, which may transmit only a portion of the re-polarized light, depending on the particular polarization output from the electro-optical switch. Remaining portions of the re-polarized light may be reflected and discarded (e.g., absorbed by a beam dump material). In some cases, the electro-optical material may switch between "on" and "off" conditions within a time span of a few nanoseconds to a few microseconds.

In a specific embodiment, illumination power control element 130 includes a high-speed electrically-controlled optical shutter, known as a Pockels Cell. A Pockels Cell may be set in an "on" condition to allow the light generated by illumination source 101 to pass freely. When the presence of a large particle is detected, the Pockels Cell may be switched to an "off" condition to change the polarization of the generated light to a different polarization, which can be at least partially filtered out by a polarizing beam splitter. To switch between the "on" and "off" conditions, an electrical voltage provided by a variable power supply may be supplied to the Pockels Cell to change the polarization of the light passed through the electro-optical material (typically, an electro-optical crystal). The voltage supplied to the Pockels Cell may be determined by control signal 133 communicated from computing system 140.

An AOM can be driven at any suitable frequency, and thus modulate illumination power over a broad range. In another example, a Pockels Cell can be driven to produce substantially any phase shift, and thus, may be combined with a polarizing beam splitter to create substantially any output power level. In some embodiments, circuitry and/or software may be included with illumination power control element 130 to provide a continuous power level adjustment (e.g., in the form of a closed feedback loop).

In some embodiments, illumination power control element 130 includes a combination of discrete optical density filters that are selectively inserted into the beam path based on control commands 133 received from computing system 140.

In general, the present invention may encompass any appropriate technique for dynamically altering the power level of an illumination source provided that the power control element provides a relatively fast response and sufficient dynamic range. In some examples, beam power is modulated at sub-second timescales to illuminate a metal particle with high power to initiate oxidation, then immediately lowering power to continue absorption by the oxide at the illumination wavelength without damaging the oxidized particle.

As depicted in FIG. 1, illumination light 117 is also polarized by polarizing element 131. Some illumination sources, such as lasers, intrinsically emit polarized light. In some embodiments, it is preferable to polarize the illumination light and cross-polarize the collected light (e.g., with analyzer 132) to improve the signal to noise ratio of the detected signals. In these embodiments, it is preferable to polarize the illumination light at a predetermined orientation angle with respect to one or more crystal axes of the substrate (e.g., single crystal silicon, etc.) underlying the defect particle and cross-polarize the collected light at an orthogonal angle with respect to the illumination light to suppress background noise from the substrate and enhance the signal to noise ratio of the defect signal.

In some other embodiments the illumination light is polarized at different orientation angles with respect to one or more crystal axes of the defect particle. In some examples, the incident polarization and analyzer directions may be changed and spectra collected for each for a set of orientation angles. The spectral responses are analyzed to confirm whether a particle defect is crystalline, aid the identification of its composition, or identify defect class membership. It is noted that gathering a set of measurement data at different illumination and collection polarization angles from a defect particle is time consuming and comes at a cost of decreased throughput.

After passing through illumination power control element 130, the illumination beam 117 is directed to a beam splitting element 113 that directs a portion of the illumination beam 119 toward objective 114. In some embodiments, beam splitting element 113 is a dichroic beam splitter. However, in general, any suitable beam splitter may be contemplated within this patent document.

Objective 114 focuses the illumination beam 119 onto wafer 110 at measurement spot 106. As described hereinbefore, wafer positioning system 125 moves wafer 110 the projection of illumination beam 119 onto the wafer surface over measurement spot 106. Motion controller 123 coordinates the rotation of wafer 110 by rotation stage 121 and the translation of wafer 110 by translation stage 122 to achieve the desired positioning of wafer 110 within the field of view of the defect particle activation and analysis subsystem.

In the embodiment depicted in FIG. 1, objective 114 collects light scattered and/or reflected from wafer 110 in response to illumination beam 119 over a range of collection angles at measurement spot 106. The collected light 120 passes through beam splitting element 113.

In some embodiments, the defect particle activation and analysis subsystem is configured to perform a Raman analysis of the collected light. In these embodiments, it is preferable to filter the collected light 120 by one or more spectral filters 115 that filter out Rayleigh wavelengths from the collected light 120. In this manner, the relatively small Raman signature can be separated from the relatively large Rayleigh (i.e., elastic scattering) response of the defect particle. The one or more spectral filters may be bandpass filters and/or edge filters and/or notch filters.

In a further aspect, the defect particle activation and analysis subsystem is configured to cross-polarize the illumination and collected light to improve the signal to noise ratio of the detected signals. As depicted in FIG. 1, collected light 120 is polarized by analyzer 132 with a polarization that is orthogonal to the polarization of the illumination light 118 provided by polarizing element 131. In general, any suitable polarizing optical element may be contemplated within the scope of this patent document.

Finally, collected light 120 is projected onto a detecting surface of spectrometer 116. Spectrometer 116 generally functions to measure the detected light in a wavelength or energy resolved manner. Spectrometer 116 communicates electrical signals 135 indicative of the measured spectra to computing system 140 for further analysis of the material composition of the defect particle under measurement. In general, the detector of spectrometer 116 may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may employed to increase the signal-to-noise ratio and throughput of the system. However, other detectors such as charge-coupled device (CCD) cameras, arrays of photodiodes, phototubes and photomultiplier tubes (PMTS) may be used, depending on the amount of light available for inspection and the type of inspection being performed.

In one aspect, a defect particle activation and analysis subsystem of a surface inspection tool is configured to activate observable Raman bands of a defect particle by laser-assisted thermal oxidation and perform a Raman spectroscopic measurement of the activated particle. Many metallic nanoparticles have no observable Raman spectral lines because of their body centered cubic (bcc) or face centered cubic (fcc) crystal symmetry. In one important example, metallic copper (Cu) has a fcc crystal structure.

Figure 5:
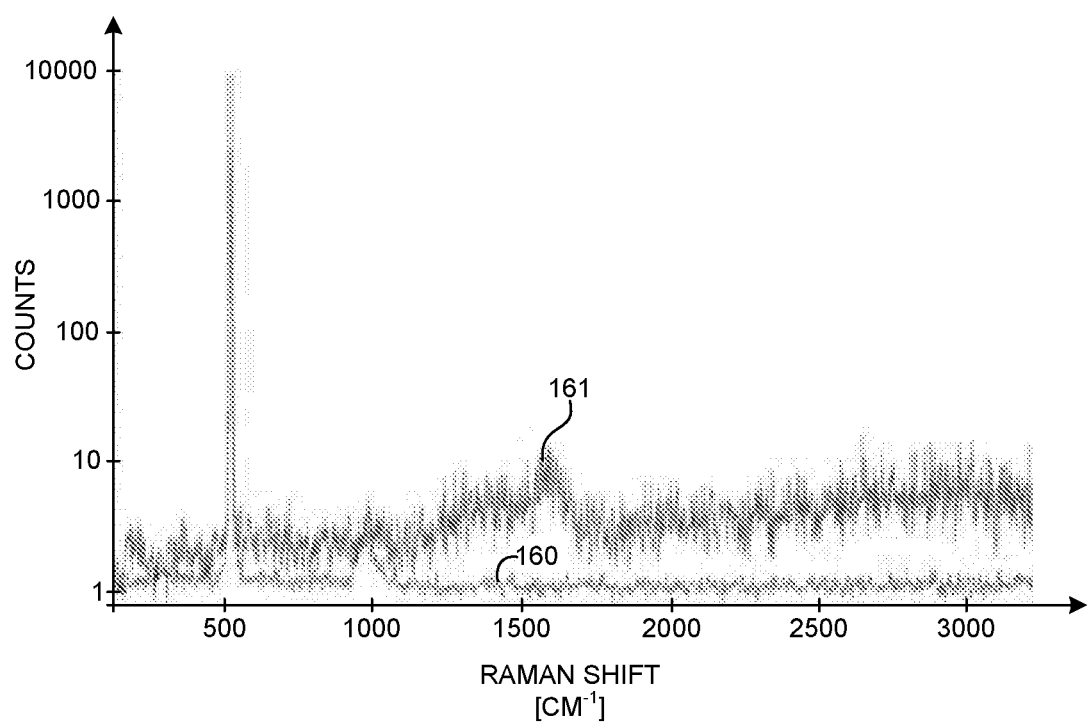
FIG. 5 is a diagram illustrative of spectral measurements of a defect particle activated at a low illumination power level.

FIG. 5 depicts spectral measurements collected by the defect particle activation and analysis subsystem of surface inspection system 100 at low illumination power. In this example, illumination source 111 supplied approximately 0.01 milliwatts of illumination power at 405 nanometer wavelength onto the surface of wafer 110 over a measurement spot size of approximately one micrometer diameter. The spectral measurement results were integrated over a 100 second measurement period. Plotline 160 depicts the measured spectrum of the wafer surface without a particle in the laser illumination spot. Plotline 161 depicts the measured spectrum of the wafer surface with a copper particle of 945 nanometers diameter in the laser illumination spot. As depicted in FIG. 5, weak Raman bands indicative of graphitic carbon are visible, but there is no evidence of any Raman bands despite integrating for 100 seconds. Thus, the amount of oxidized copper, if any, is too small to yield an identifiable Raman spectrum.

Figure 6:
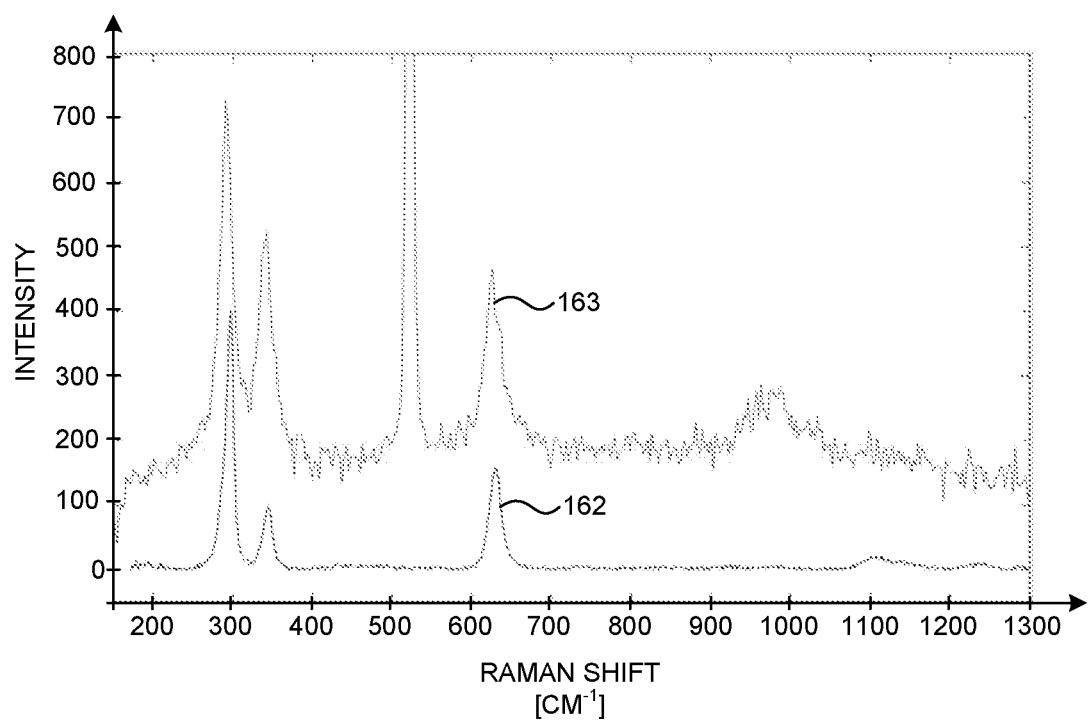
FIG. 6 is a diagram illustrative of spectral measurements of a defect particle activated at a high illumination power level.

FIG. 6 depicts spectral measurements collected by the defect particle activation and analysis subsystem of surface inspection system 100 at high illumination power. In this example, illumination source 111 supplied approximately 10 milliwatts of illumination power at 405 nanometer wavelength onto the surface of wafer 110 over a measurement spot size of approximately one micrometer diameter. The spectral measurement results were integrated over a 50 second measurement period. Plotline 163 depicts the measured spectrum of the wafer surface with a copper particle of 945 nanometers diameter in the laser illumination spot. Plotline 162 depicts a reference spectrum of CuO. By comparison with the reference spectrum, a strong Raman response of cupric oxide (CuO) is clearly visible in the measurement results depicted in plotline 163. Thus, after activation (e.g., laser-assisted thermal oxidation), the Raman response indicative of a cupric oxide chemical composition is clearly visible.

Furthermore, the measured spectra depicted in FIG. 6 were measured by cross-polarizing the collected light with the illumination light as described hereinbefore. By cross-polarizing the measured spectra with the illumination light, the first order phonon peak and the second order phonon peak associated with the silicon substrate (520 cm$^{-1}$ and 1000 cm$^{-1}$, respectively) are suppressed. In addition, background signals associated with multiphonon scattering are also suppressed, resulting in enhanced CuO peaks in the measured spectra. In some examples, cross-polarization, as described herein enhances the signal to noise ratio (SNR) of the detected Raman bands in a range of wavenumbers between 200 cm$^{-1}$ and 1000 cm$^{-1}$.

Figure 7:
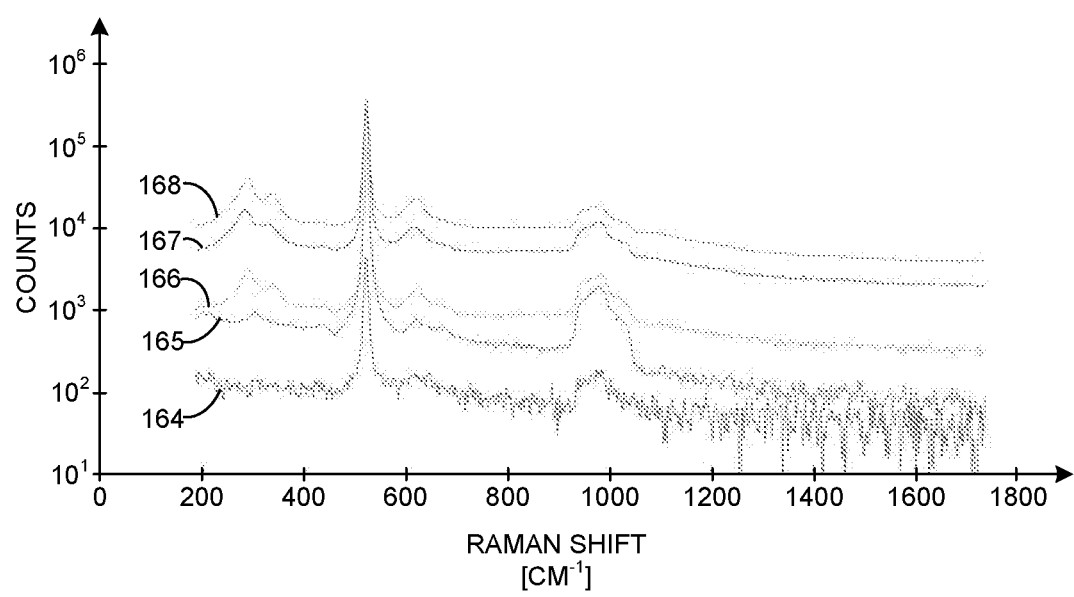
FIG. 7 is a diagram illustrative of spectral measurements of a defect particle activated at different illumination power levels.

FIG. 7 depicts spectral measurements collected by the defect particle activation and analysis subsystem of surface inspection system 100 at different illumination power levels. In these examples, illumination source 111 supplied different levels of illumination power at 405 nanometer wavelength onto the surface of wafer 110 over a measurement spot size of approximately one micrometer diameter. One hundred scans, each with one second of exposure time, are averaged to realize the depicted results. Plotline 164 depicts exposure power of 0.1 milliwatts. Plotline 165 depicts exposure power of 0.5 milliwatts. Plotline 166 depicts exposure power of 1 milliwatt. Plotline 167 depicts exposure power of 5 milliwatts. Plotline 168 depicts exposure power of 10 milliwatts. As depicted in FIG. 7, as illumination power increases, the Raman response associated with CuO increases in magnitude. In general, the response is practically undetectable at 0.1 milliwatt exposure, but begins to become detectable at 1.0 milliwatt exposure.

The results show no evidence of CuO peaks in the series taken at 0.1 or 0.5 milliwatt power. CuO peaks are clearly discernable at 1 milliwatt power, and stronger peaks are observed at 5 and 10 milliwatts power. The summed spectra depicted in FIG. 7 illustrate that the size of the CuO peak progressively grows relative to peaks associated with the first and second order phonon peaks associated with silicon.

Optical micrograph images of the copper particle collected before and after activation reveal changes in the particle corresponding with changes observed in the spectral series. After the 0.1 and 0.5 milliwatt measurements, there were no discernable changes in the size of the particle. However, the particle size increased after the 1, 5, and 10 milliwatt measurements. In principle, the cupric oxide unit cell has a 74% larger volume than metallic copper. A micrograph image of the particle after activation with 10 milliwatts illumination showed a 56% increase in diameter, which represents an increase in volume of approximately 45%.

It is quite reasonable that a 10 milliwatt laser beam, focused to a spot size of approximately one micrometer, can heat a small copper particle to 150-1500 C, driving oxidation in ambient atmosphere.

Consider an isolated spherical copper particle in vacuum, in thermal equilibrium with the surroundings at absolute temperature, $T_0$. In this state, the rates of radiative emission and absorption are balanced, according to the Stefan-Boltzmann law illustrated in equation (1), $$P_{abs,o} = P_{rad,o} = \sigma \varepsilon A T_0^4 \tag{1}$$

where A is the surface area of the sphere, $\varepsilon$, is the emissivity of the surface, and, $\sigma$, is the Stefan-Boltzmann constant ($5.67 \times 10-8$ W/m$^2$*K$^4$).

Figure 3:
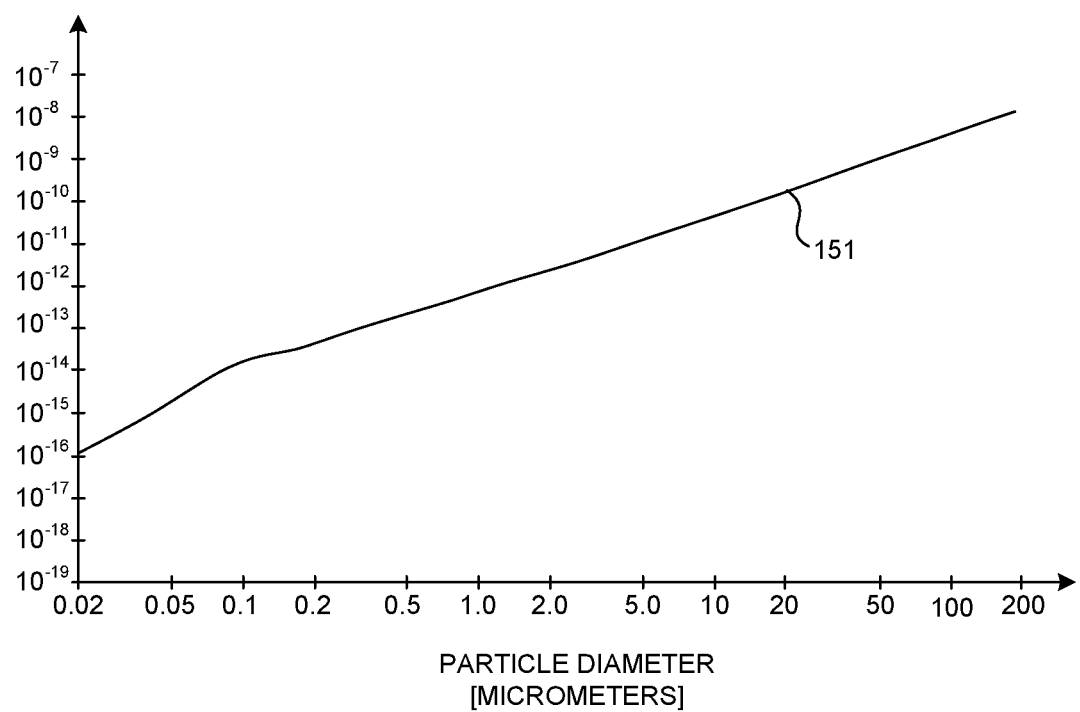
FIG. 3 is a diagram illustrative of a simulation of the absorption cross-section of a copper particle as a function of sphere diameter.

When illuminated by 405 nm light, the complex index of refraction of copper is 1.301+2.129i. FIG. 3 depicts the absorption cross-section of the copper particle as a function of sphere diameter, calculated in accordance with Mie theory. For a copper sphere of 180 nanometer diameter, the absorption cross-section, $C_{abs}$, is $3.91 \times 10^{-10}$ cm$^2$. At 10 milliwatt exposure over a 1 micrometer spot size, the irradiance, $I_0$, is 1 MW/cm$^2$. Under these conditions the thermal absorption of the copper sphere is illustrated in equation (2), $$P_{abs,I} = C_{abs} I_0 = 3.76 \times 10^{-4} \text{ W} \tag{2}$$

which is 3.9% of the total 10 milliwatts of laser power. The absorbed energy is converted to heat, and the particle temperature rises.

For a sphere completely surrounded by a fluid, heat flow Q between a sphere and the surrounding fluid is given by equation (3), $$Q = 2\pi k d (T - T_0) \tag{3}$$

where d is the sphere diameter, T is the temperature of the surface of the sphere, $T_0$ is the temperature of the air far from the sphere, and k is the thermal conductivity of the fluid. For a particle on a substrate, it is reasonable to write equation (7) in terms of an effective thermal conductivity, k=$k_{eff}$, which takes a value that is greater that the thermal conductivity of air, but less than the conductivity of the substrate. The exact value depends on the extent of the thermal contact of the particle with the substrate.

Figure 4:
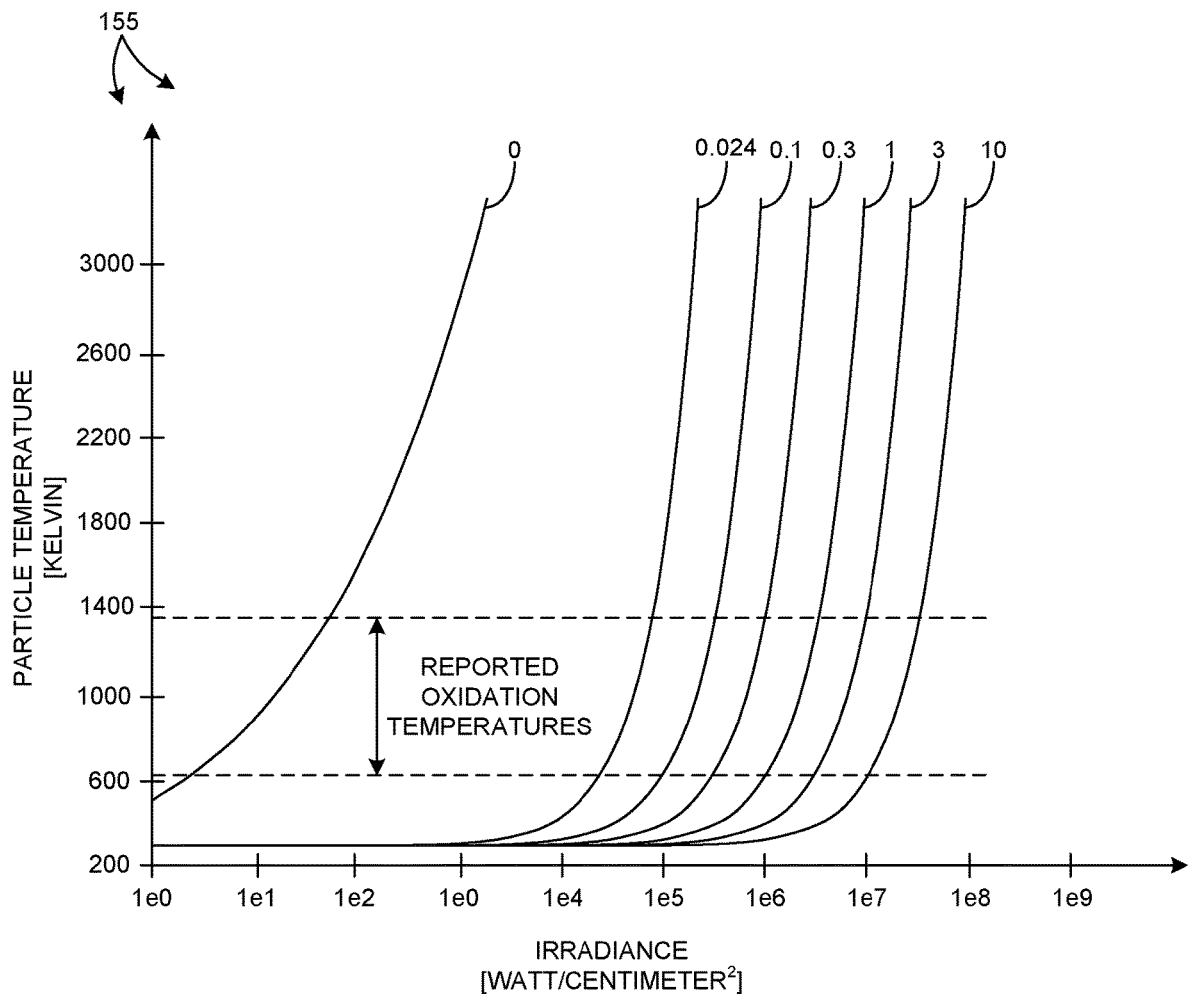
FIG. 4 is a diagram illustrative of a simulation of the thermal heating of a copper particle deposited on the surface of a silicon wafer as a function of incident irradiance and various values of effective thermal conductivity.

The value of $k_{eff}$ can be specified more narrowly by adding equation (3) to the right hand side of the heat balance illustrated by equation (1). This results in a quartic equation illustrated in equation (4), $$T^4 + \alpha T - \beta = 0 \qquad (4)$$

where $\alpha = 2k_{eff}/\sigma \varepsilon d$ and $\beta = \alpha T_0 + T_0^4 + C_{abs}I_0/\sigma \varepsilon A$. FIG. 4 depicts a plot 155 representative the solution of Equation (4) for T as a function of incident irradiance, $I_0$, for various values of $k_{eff}$. The value of $k_{eff}$ associated with each plotline is illustrated in FIG. 4. Each plotline represents the steady state temperature of an irradiated, copper sphere of 180 nanometer diameter. In vacuum, $k_{eff}$ is zero valued. As depicted in FIG. 4, it would take less than 1 W/cm² to heat the particle sufficiently to initiate oxidation (assuming trace oxygen molecules in the vacuum). In air, $k_{eff}$ is approximately 0.024. In air, it takes $10^4$-$10^5$ W/cm² to reach oxidizing conditions. However, in actual operating conditions, $k_{eff}$ must be larger because the measured copper particle did not liquefy and disappear at 1 MW/cm². Thus, it seems most likely that the value of $k_{eff}$ for copper particles on silicon substrates is between 0.3 and 1 W/(m*K), where 1 MW/cm² heats the particle to approximately 1,300K and 600K, respectively.

As a relatively reactive metal, finely divided copper nanoparticles are oxidized by exposure to the laser illumination. As depicted in FIGS. 5-7, cupric oxide is identifiable from its known vibrational Raman spectra. Surface inspection system 100 also includes various electronic components (not shown) needed for processing the scattered signals detected by the detectors. For example, system 100 may include amplifier circuitry to receive signals from the detectors and to amplify the signals by a predetermined amount. In some embodiments, an analog-to-digital converter (ADC) (not shown) is included to convert the amplified signals into a digital format suitable for use within computing system 140. In one embodiment, the processor 141 may be coupled directly to an ADC by a transmission medium. Alternatively, the processor 141 may receive signals from other electronic components coupled to the ADC. In this manner, the processor may be indirectly coupled to the ADC by a transmission medium and any intervening electronic components.

In general, computing system 140 is configured to detect features, defects, or light scattering properties of the wafer using electrical signals obtained from each detector. The computing system 140 may include any appropriate processor(s) known in the art. In addition, the computing system 140 may be configured to use any appropriate defect detection algorithm or method known in the art. For example, the computing system 140 may use a die-to-database comparison or a thresholding algorithm to detect defects on the specimen.

In addition, inspection system 100 may include peripheral devices useful to accept inputs from an operator (e.g., keyboard, mouse, touchscreen, etc.) and display outputs to the operator (e.g., display monitor). Input commands from an operator may be used by computing system 140 to adjust threshold values used to control illumination power. The resulting power levels may be graphically presented to an operator on a display monitor.

Inspection system 100 includes a processor 141 and an amount of computer readable memory 142. Processor 141 and memory 142 may communicate over bus 143. Memory 142 includes an amount of memory 144 that stores a program code that, when executed by processor 141, causes processor 141 to execute the defect activation and composition analysis functionality described herein.

In a further aspect, computing system 140 is configured to receive spectroscopic measurement results collected from an activated particle and estimate a composition of the particle based on the measurements. In some embodiments, computing system 140 matches the spectroscopic signature of the measured spectra (e.g., peak locations, peak magnitudes, etc.) with the signature of reference spectra measured from particles having a known composition. In some embodiments, computing system 140 matches the spectroscopic signature of the measured spectra with the signature of analytically derived spectra. In some embodiments, computing system 140 correlates the spectroscopic signature of the measured spectra with a library database of previously analyzed defect particles. In some embodiments, the library includes optical spectroscopic response data. In some further embodiments, the library also includes other composition data (e.g., photoluminescence data, energy dispersive X-ray (EDX) spectrometer data, etc.). In some embodiments, computing system 140 assigns a classification code to the particle that best matches a classification code associated with the closest spectral match in the library. In this manner, the composition of the measured defect particle is identified with a defect classification code that most closely matches the measured spectra.

In general, the optical spectroscopic signatures of a transformed particle can be observed with one of more of a plurality of optical spectroscopic methods including, but not limited to: spontaneous Raman spectroscopy; stimulated Raman spectroscopy; coherent anti-Stokes Raman spectroscopy; second harmonic generation, four-wave mixing, and other non-linear spectroscopies; fluorescence spectroscopy, also called photoluminescence (PL) spectroscopy; fluorescence lifetime time-correlated photon counting spectroscopy; Raman and/or fluorescence spectroscopies with enhanced sensitivity due to metallic nanostructures that are positioned in closed proximity to the particle being analyzed, such as in tip-enhanced Raman spectroscopy.

In a further aspect, the composition of a defect particle is determined based on the measurement of photoluminescence (PL) spectra (e.g., PL spectra measured by surface inspection system 100). In some examples, defect particles exhibit broad-band photoluminescence (PL) spectra extending as far as the near IR.

However, in some examples, PL spectra are unstable and tend to bleach out over time if excessive illumination power is employed. In another further aspect, the irradiance provided by the illumination source (e.g., illumination source 111) is initially set to a low level to acquire PL spectra to minimize bleaching that would occur if relatively high power were employed. After the acquisition of PL spectra, the irradiance is increased to spectroscopically activate the particle and acquire Raman spectral measurements. In this manner, both PL and Raman spectra are available to identify the composition of the defect particle.

Figure 8:
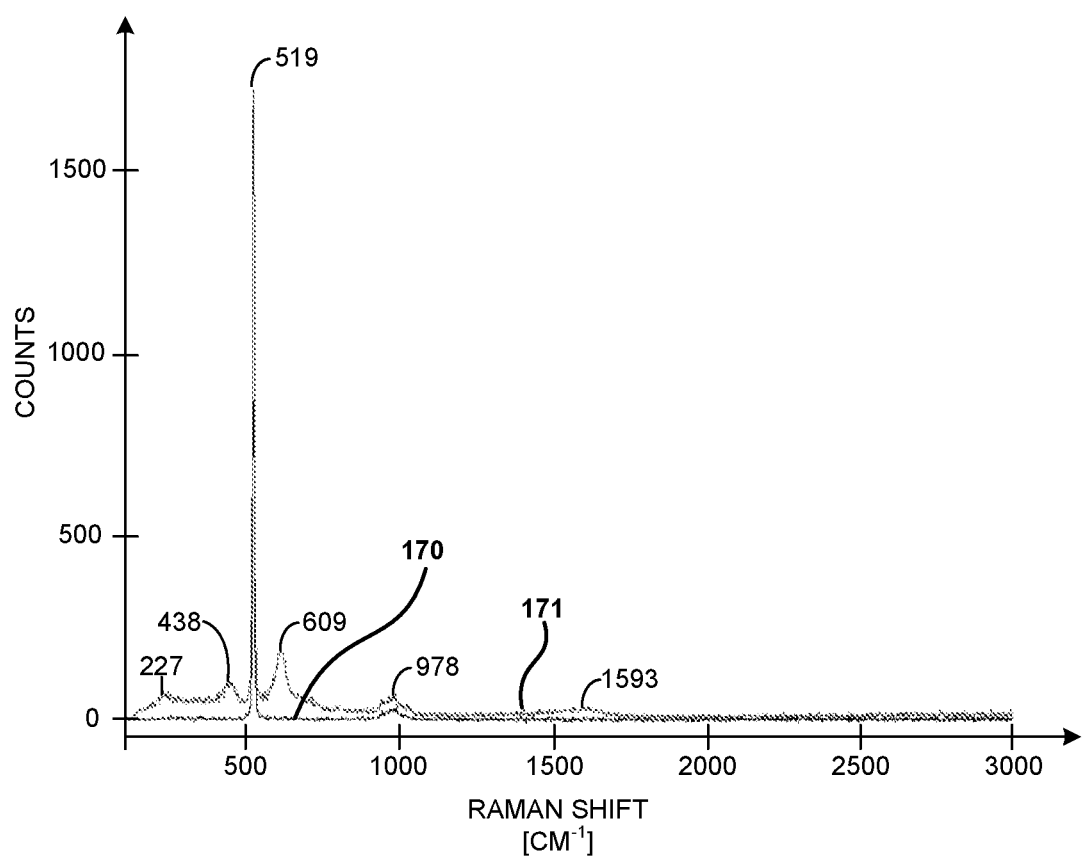
FIG. 8 is a diagram illustrative of spectral measurements of a titanium dioxide particle collected by a surface inspection system at low illumination power.
Figure 9:
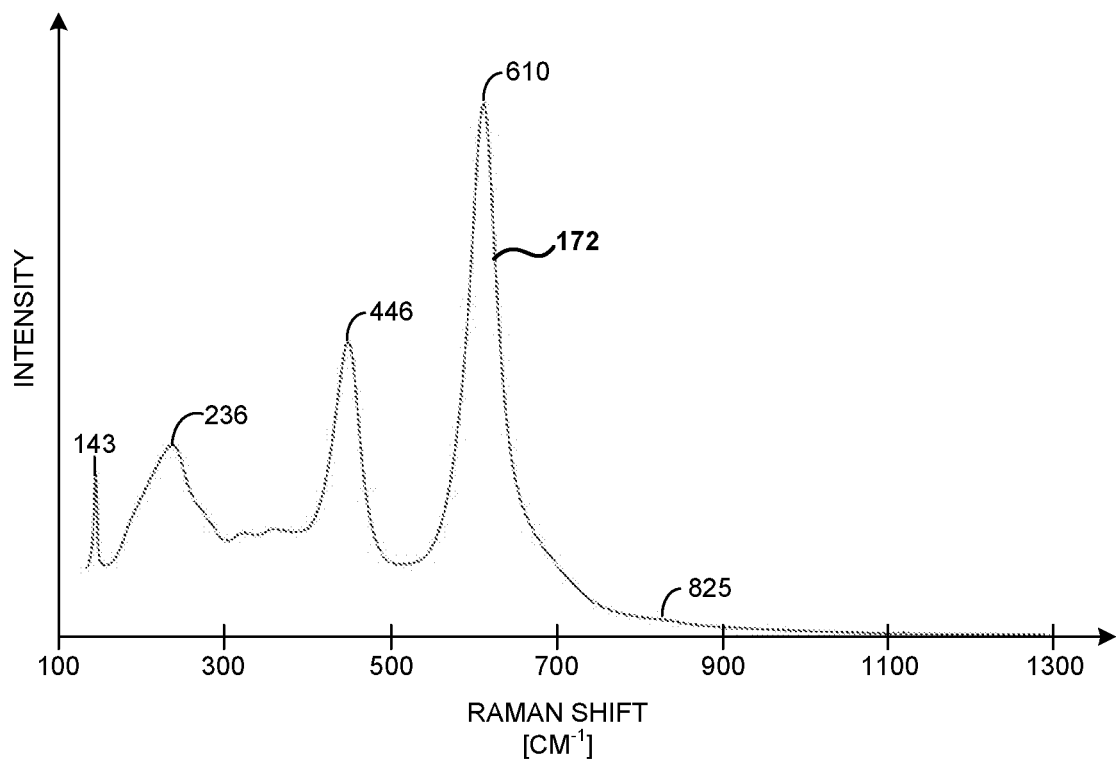
FIG. 9 is a simplified diagram illustrative of a reference Raman spectrum associated with titanium dioxide ($TiO_2$).

In some examples, defect particles exhibit Raman spectra without significant activation. FIG. 8 depicts spectral measurements collected by the defect particle activation and analysis subsystem of surface inspection system 100 at low illumination power. In this example, illumination source 111 supplied approximately 0.1 milliwatts of illumination power at 405 nanometer wavelength onto the surface of wafer 110 over a measurement spot size of approximately one micrometer diameter. The spectral measurement results were integrated over a 10 second measurement period. Plotline 170 depicts the measured spectrum of the wafer surface without a particle in the laser illumination spot. Plotline 171 depicts the measured spectrum of the wafer surface with a particle of approximately 117 nanometers diameter in the laser illumination spot. A strong Raman response of is clearly visible in the measurement results depicted in plotline 171. For reference, the wavenumbers associated with each of the major peaks are labeled in FIG. 8. FIG. 9 depicts a plotline 172 of a reference Raman spectrum associated with titanium dioxide (TiO2). For reference, the wavenumbers associated with each of the major peaks associated with the reference spectrum are labeled in FIG. 9. Comparing the measured Raman spectrum of the defect particle depicted in FIG. 8 with the reference Raman spectrum associated with TiO2 in FIG. 9, it is clear that the measured defect particle is TiO2.

Although, the measurement of a copper particle is specifically described herein, in general, surface inspection system 100 is configured to measure many different types of particles, including, but not limited to particles having organic, inorganic, or metallic chemical composition with crystalline, poly-crystalline, or amorphous structure.

In some examples, the particle under inspection is a metallic particle with a bcc or fcc crystalline structure that lacks intrinsic vibrational Raman spectroscopic signatures.

In some examples, the particle under inspection is a metallic particle with a hexagonal close packed (hcp) structure that has a very weak intrinsic vibrational Raman spectroscopic signature. In these examples, particle activation is employed to transform the particle and improve the detectability of vibrational Raman spectroscopic signatures associated with the transformed particle.

In some examples, the transformation of the particle is a chemical oxidation of a metallic particle in the ambient terrestrial atmosphere at an elevation between 0 and 10,000 feet above mean sea level.

In some examples, the transformation of the particle occurs in a chamber of controlled partial pressure of oxygen greater or less than 0.2 atmospheres. In some examples, the chamber includes additional partial pressures of substantially inert gases that do not participate in the oxidation process. Such gases include, but not limited to, nitrogen, helium, neon, argon, xenon, carbon dioxide, halogenated hydrocarbons, fluorinated metals, and non-metals such as uranium hexafluoride and sulfur hexafluoride, respectively.

In some examples, the oxidative transformation of a metallic particle is carried out with additional partial pressures of gaseous compounds that catalyze the oxidative transformation.

In some examples, the oxidative transformation of a metallic particle is carried out in a chamber with additional partial pressures of gaseous compounds that promote the formation of the metallic oxide with oxidation state and crystalline polymorphic structure having an enhanced Raman scattering cross section, relative to other possible oxidation states or polymorphs that form absent the additional gaseous compounds.

In some examples, the metallic particle is treated with a surface-active material before oxidation to promote formation of the metallic oxide with oxidation state and crystalline polymorphic structure having an enhanced Raman scattering cross section, relative to other possible oxidation states or polymorphs said metallic particle that form absent the treatment. Examples of the surface-active material include, but are not limited to, an organic amine in gas phase or dissolved in a liquid solution, or a liquid that is itself surface active and coats the metallic particle.

In some examples, the oxidative transformation is driven by elevated temperature. In some examples, the elevated temperature may be generated by radiative heating, illumination with electromagnetic radiation, or a combination thereof.

In some examples, the temperature-driven oxidative transformation is driven by the same source of electromagnetic radiation that stimulates the transformed particle to emit a spectroscopic signature that is measured and employed to identify the composition of the particle.

In some examples, the oxidative transformation of a particle is driven by a photochemical pathway stimulated by exposure to photons emitted from an electromagnetic radiation source. In some examples, the photon-driven oxidative transformation is driven by the same source of electromagnetic radiation that stimulates the transformed particle to emit a spectroscopic signature that is measured and employed to identify the composition of the particle.

In some examples, the transformation is a chemical reaction, other than an oxidative reaction, with gaseous, liquid, or solution-borne reagents and a photothermal or photochemical driving force. The driving force provided by a source of electromagnetic radiation that may be different from or the same as the source that stimulates the transformed particle to emit a spectroscopic signature that is measured and employed to identify the composition of the particle.

Although surface inspection system 100 includes an illumination source 111 that provides illumination for both particle activation and spectral measurement, in general, multiple, different illumination sources may be employed to provide illumination for activation, spectral measurement, or both. In addition, one or more illumination sources employed to map the locations of defect particles on the wafer surface (e.g., illumination source 101 depicted in FIG. 1) may also be employed to provide illumination for activation, spectral measurement, or both.

Although surface inspection system 100 includes a spectrometer 116 that performs spectral measurements of a defect particle, in general, multiple, different spectrometer subsystems may be employed to provide spectral measurements of a defect particle. In some examples, one or more beam splitting elements are included in the collection beam path to direct scattered light toward multiple spectrometers simultaneously. In some examples, a movable mirror or movable turret is employed in the collection path to direct scattered light toward multiple spectrometers sequentially.

Although spectral measurement results with illumination light at 405 nanometers were described with reference to FIGS. 5-9, in general, one or more different wavelengths of illumination light may be employed to improve the signal to noise ratio of the spectral measurements.

In some embodiments, multiple, different wavelengths are employed and the wavelengths are selected because they are known to interact with surface asperities of the substrate wafer (e.g., thin films, high aspect ratio protrusions of highly non-spherical defect particles, etc.). The surface asperities produce enhanced electromagnetic fields in their immediate vicinity that enhance weak spectroscopic signatures. In some embodiments, a surface inspection system (e.g., surface inspection system 100) includes a source of visible electromagnetic radiation having a wavelength between 600 and 700 nm. Light in this range of wavelengths is known to excite local surface plasmon resonances in high aspect ratio protrusions and features of non-spherical copper nanoparticles. The enhanced electromagnetic fields associated with the excited plasmons enhance the Raman scattering signature from a thin layer of cuprous oxide, cupric oxide, or both, on the surface of the copper nanoparticle. In some examples, the oxide layer is present in sufficient quantity on the surface of the defect particle with minimal, or no additional activation.

Figure 10:
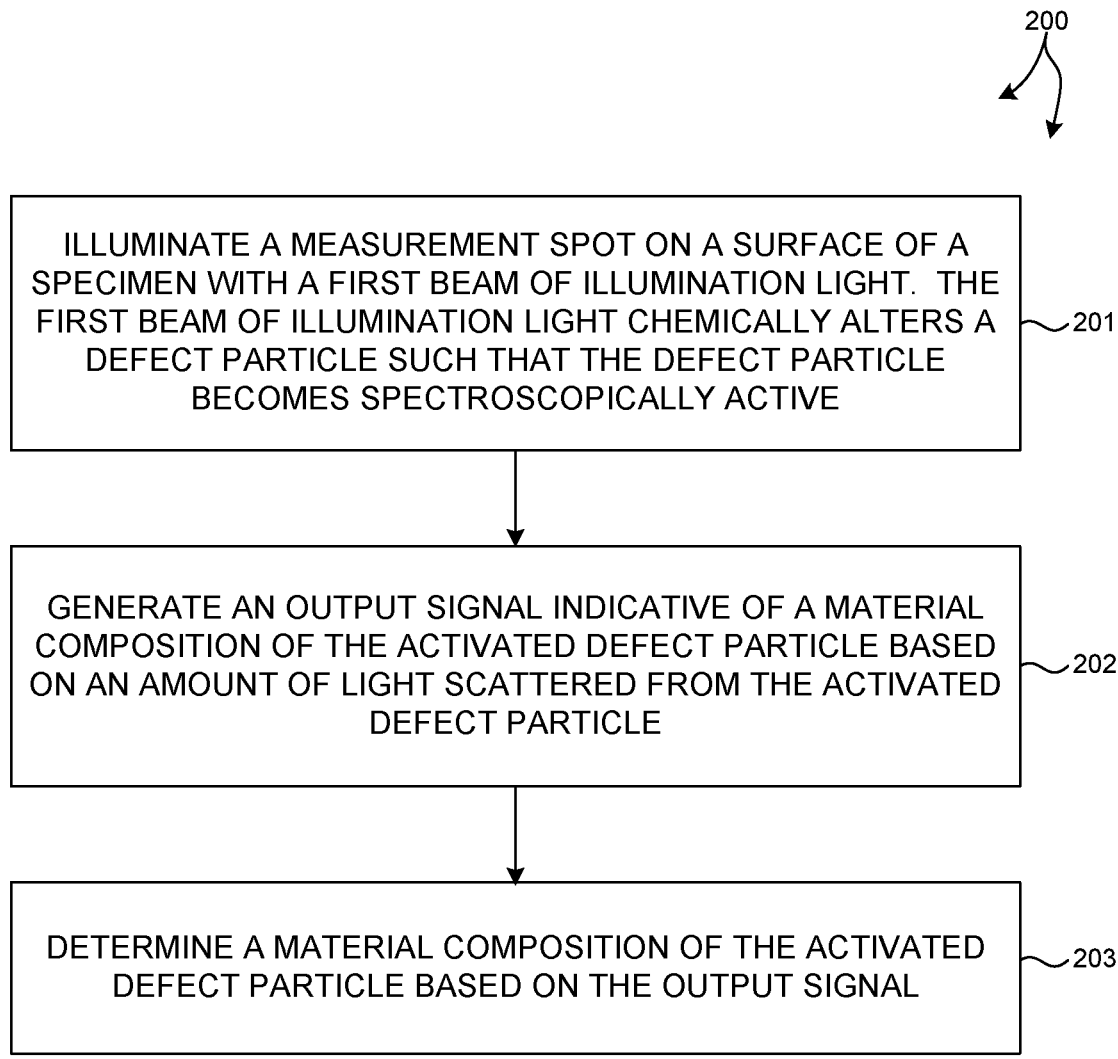
FIG. 10 illustrates a flowchart of an exemplary method 100 useful for identifying the material composition of activated defect particles on a wafer surface.

FIG. 10 illustrates a flowchart of an exemplary method 200 useful for identifying the material composition of activated defect particles as described herein. In some non-limiting examples, inspection system 100 described with reference to FIG. 1 is configured to implement method 200. However, in general, the implementation of method 200 is not limited by the specific embodiments described herein.

In block 201, a measurement spot on a surface of a specimen is illuminated with a beam of illumination light. The beam of illumination light chemically alters a defect particle such that the defect particle becomes spectroscopically active.

In block 202, an output signal indicative of a material composition of the activated defect particle is generated based on an amount of light scattered from the activated defect particle.

In block 203, a material composition of the activated defect particle is determined based on the output signal.

Various embodiments are described herein for an inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can. be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A surface inspection system comprising:
a wafer positioning system including a wafer chuck, the semiconductor wafer removeably attached to the wafer chuck, the semiconductor wafer comprising a substrate material having a crystalline structure characterized by one or more crystal axes;
an illumination source configured to generate a beam of illumination light;
one or more optical elements configured to focus the beam of illumination light to a measurement spot incident on a surface of the semiconductor wafer, wherein the wafer positioning system locates the surface of the semiconductor wafer with respect to the incident beam of illumination light;
one or more defect particle detectors configured to generate a plurality of defect output signals each defect output signal indicative of the presence of a detected defect particle within the measurement spot as the wafer positioning system scans the surface of the semiconductor wafer across the measurement spot, each detected defect particle of a plurality of detected defect particles is located at a different position on the surface of the semiconductor wafer;
a computing system configured to:
receive the plurality of defect output signals;
generate a map of the plurality of detected defect particles, the map indicating a position of each detected defect particle on the surface of the semiconductor wafer; and
communicate a control command to the wafer positioning system that causes the wafer positioning system to locate the semiconductor wafer such that the measurement spot is incident on the surface of the semiconductor wafer at a position of a detected defect particle of the plurality of detected defect particles for a period of time, wherein the incidence of the beam of illumination on the detected defect particle chemically alters the detected defect particle such that the detected defect particle becomes spectroscopically active during the period of time; and
one or more spectrometers configured to generate an output signal indicative of a material composition of the activated detected defect particle based on an amount of light scattered from the activated detected defect particle in response to the incidence of the beam of illumination on the detected defect particle for the period of time, the computing system further configured to:
    receive the output signal indicative of the amount of light scattered from the activated detected defect particle; and
    determine a material composition of the activated detected defect particle based on the output signal.

2. The surface inspection system of claim 1, further comprising:
    a first polarizing element located in an optical path of the beam of illumination light, the first polarizing element configured to polarize the beam of illumination light in a first direction; and
    a second polarizing element located in an optical path of the amount of light scattered from the activated detected defect particle, the second polarizing element configured to polarize the amount of light scattered from the activated detected defect particle in a second direction that is orthogonal to the first direction.

3. The surface inspection system of claim 2, wherein the first polarizing element is oriented with respect to a direction of a crystal axis of the one or more crystal axes of the substrate material of the semiconductor wafer such that the beam of illumination light is focused onto the measurement spot at a predetermined polarization orientation angle with respect to the crystal axis of the substrate material.

4. The surface inspection system of claim 1, further comprising:
    a library database of measurements of previously analyzed detected defect particles stored in a memory, the computing system further configured to correlate the output signal indicative of light scattered from the activated detected defect particle with a plurality of measurements of previously analyzed detected defect particles of the library database to determine the material composition of the activated detected defect particle.

5. The surface inspection system of claim 1, wherein the detected defect particle has an organic, inorganic, or metallic chemical composition with crystalline, poly-crystalline, or amorphous structure.

6. The surface inspection system of claim 1, wherein the detected defect particle is a metal with a face centered cubic crystalline structure or a body centered cubic crystalline structure that does not exhibit an intrinsic vibrational Raman spectroscopic signature, or a hexagonal close packed crystalline structure that weakly exhibits an intrinsic vibrational Raman spectroscopic signature.

7. The surface inspection system of claim 1, wherein the detected defect particle is metallic and the detected defect particle is chemically altered by chemical oxidation to become spectroscopically active.

8. The surface inspection system of claim 7, further comprising:
    an environmental chamber including a controlled partial pressure of oxygen different from a partial pressure of oxygen in an ambient environment surrounding the surface inspection system, wherein the chemical oxidation occurs in the environmental chamber.

9. The surface inspection system of claim 7, wherein the detected defect particle is coated with a surface-active material before the beam of illumination light is projected onto the detected defect particle, wherein the surface-active material promotes the chemical oxidation.

10. The surface inspection system of claim 1, wherein the output signal indicative of the material composition of the activated detected defect particle includes an observable Raman spectrum.

11. The surface inspection system of claim 1, wherein the output signal indicative of the material composition of the activated detected defect particle includes an observable photoluminescent spectrum.

12. The surface inspection system of claim 1, wherein the illumination source is configured to generate illumination light having multiple, distinct wavelengths.

13. The surface inspection system of claim 1, further comprising:
    a rotatable polarizing element located in an optical path of the second beam of illumination light, the rotatable polarizing element configured to orient the polarizing element at a plurality of different polarization orientation angles with respect to the semiconductor wafer, and wherein the output signal indicative of the material composition of the activated detected defect particle is generated based on the amount of light scattered from the activated detected defect particle in response to the incidence of the beam of illumination light on the activated detected defect particle at each of the plurality of different polarization angles.

14. The surface inspection system of claim 1, further comprising:
    an illumination power control element located in an optical path between the illumination source and semiconductor wafer, wherein the illumination power control element changes an illumination power of the beam of illumination light during the period of time the measurement spot is incident on the surface of the semiconductor wafer at the position of the detected defect particle of the plurality of detected defect particles.

15. A method comprising:
    illuminating a defect particle on a surface of a semiconductor wafer with a beam of illumination light for a first period of time;
    generating a first output signal based on an amount of light scattered from the defect particle in response to the beam of illumination light during the first period of time, wherein the first output signal includes an observable photoluminescent spectrum indicative of a material composition of the defect particle;
    illuminating the defect particle on the surface of the semiconductor wafer with the beam of illumination light for a second period of time after the first period of time, wherein an illumination power of the beam of illumination light is higher during the second period of time than during the first period of time, wherein the beam of illumination light chemically alters the defect particle during the second period of time such that the defect particle becomes spectroscopically active, wherein a Raman spectral response is not observable before the defect particle becomes spectroscopically active and a Raman spectral response is observable after the defect particle becomes spectroscopically active;
    generating a second output signal indicative of a material composition of the activated defect particle based on an amount of light scattered from the activated defect particle in response to the beam of illumination light during the second period of time; and
    determining a material composition of the activated defect particle based on the first and second output signals.

16. The method of claim 15, wherein the defect particle is metallic and the defect particle is chemically altered by chemical oxidation to become spectroscopically active.

17. The method of claim 15, wherein the second output signal indicative of the material composition of the activated defect particle includes an observable Raman spectrum.

18. The method of claim 15, further comprising:
polarizing the beam of illumination light in a first direction; and
polarizing the amount of light scattered from the activated defect particle in a second direction that is orthogonal to the first direction.

19. A surface inspection system comprising:
a defect particle detection subsystem configured to project a beam of illumination light onto a surface of a specimen at a measurement spot during a first period of time and detect the presence of the defect particle at the measurement spot based on an amount of light scattered from the defect particle in response to the illumination of the defect particle by the beam of illumination light during the first period of time; and
a defect particle activation and analysis subsystem configured to project the beam of illumination light onto the measurement spot during a second period of time after the first period of time to chemically alter the defect particle such that the defect particle becomes spectroscopically active, wherein a Raman spectral response is not observable before the defect particle becomes spectroscopically active and a Raman spectral response is observable after the defect particle becomes spectroscopically active, and determine a material composition of the activated defect particle based on an amount of light scattered from the activated defect particle in response to the beam of illumination light during the second period of time.

* * * * *